(12) United States Patent
Heinritz-Adrian

(10) Patent No.: US 7,678,956 B2
(45) Date of Patent: Mar. 16, 2010

(54) METHOD FOR CATALYTICALLY DEHYDRATING PROPANE TO FORM PROPYLENE

(75) Inventor: Max Heinritz-Adrian, Munster (DE)

(73) Assignee: Uhde GmbH, Dortmund (DE)

( * ) Notice: Subject to any disclaimer, the term of this patent is extended or adjusted under 35 U.S.C. 154(b) by 65 days.

(21) Appl. No.: 11/667,518

(22) PCT Filed: Nov. 10, 2005

(86) PCT No.: PCT/EP2005/012070

§ 371 (c)(1),
(2), (4) Date: Feb. 19, 2008

(87) PCT Pub. No.: WO2006/050957

PCT Pub. Date: May 18, 2006

(65) Prior Publication Data

US 2008/0300440 A1    Dec. 4, 2008

(30) Foreign Application Priority Data

Nov. 11, 2004  (DE) .................. 10 2004 054 657

(51) Int. Cl.
*C07C 5/333* (2006.01)

(52) U.S. Cl. .................. 585/659; 585/654; 585/658; 585/660; 585/661; 585/662; 585/663

(58) Field of Classification Search .................. 585/654, 585/658, 659–663

See application file for complete search history.

(56) References Cited

U.S. PATENT DOCUMENTS

| | | | |
|---|---|---|---|
| 4,599,471 A | | 7/1986 | Ward |
| 4,990,632 A | * | 2/1991 | Ramachandran et al. ..... 549/523 |
| 5,233,118 A | * | 8/1993 | Bricker et al. ............... 585/660 |
| 5,235,121 A | | 8/1993 | Brinkmeyer et al. |
| 5,997,826 A | | 12/1999 | Lodeng et al. |
| 2006/0122448 A1 | | 6/2006 | Thiagarajan et al. |
| 2006/0128989 A1 | | 6/2006 | Dubois et al. |

FOREIGN PATENT DOCUMENTS

| | | |
|---|---|---|
| DE | 1 98 58 747 A1 | 6/2000 |
| EP | 0 799 169 B1 | 3/2000 |
| EP | 1 016 641 A1 | 7/2000 |
| WO | WO 96/33150 A1 | 10/1996 |
| WO | WO 2004/024666 A1 | 3/2004 |
| WO | WO 2004/039920 A2 | 5/2004 |

* cited by examiner

*Primary Examiner*—In Suk Bullock
(74) *Attorney, Agent, or Firm*—Marshall & Melhorn, LLC

(57) ABSTRACT

The invention relates to a method for producing propylene during which a first gas mixture, which is technically free of oxygen but contains propane, water vapor and hydrogen, and which has a temperature of at least 400° C., is led into a reaction device having at least one catalyst bed as well as usual dehydration conditions. Another gas mixture, which contains propane and oxygen and which can also contain ammonia, the propane content exceeding the oxygen content, is led into the same reaction device in which it reacts with the first gas mixture while forming propylene, water vapor and hydrogen, and the formed gas mixture containing propylene, water vapor and hydrogen is drawn out of the reaction device.

9 Claims, 2 Drawing Sheets

METHOD FOR CATALYTICALLY DEHYDRATING PROPANE TO FORM PROPYLENE

BACKGROUND OF THE INVENTION

The invention relates to a process for catalytic dehydration of propane to form propylene in accordance with the following formula:

$$C_3H_8 \leftrightarrow C_3H_6 + H_2 \tag{1}$$

from various sources of propane, which may also contain other gas components. The chemical reaction (1), which normally takes place in a gaseous phase at a temperature ranging from 540° C. to 820° C., is a strong endothermic equilibrium reaction the conversion rates of which are subject to thermodynamic limits and which depend on the specific partial pressures and the temperature. The dehydration reaction is promoted by low partial pressures of the hydrocarbons and by high temperatures. Cracked products form in side reactions and cause deposits of hydrocarbons on the catalyst so that the latter is deactivated and thus requires a cyclic regeneration during plant operation.

If dehydration takes place in a catalyst bed operated in an adiabatic manner, the endothermic reaction causes a gradual temperature drop over the whole length of the catalyst bed. Hence, the conversion rate in the catalyst bed is restricted to a certain degree so that several catalyst beds are required to obtain the high conversion rates desired and re-heating must be provided downstream of each catalyst bed.

The catalytic dehydration of paraffin to obtain olefin may in fact take place in heated or isothermal catalyst beds, too. U.S. Pat. No. 5,235,121, for example, describes a process in which the input mixture consists of light paraffins and water vapour and is fed to a tubular reactor with external firing, i.e. the catalyst bed is a heated fixed bed. The catalyst used in that process is of such a nature that the presence of water vapour cannot initiate a steam reforming process, i.e. there is no reaction of hydrocarbons with water vapour producing CO, $CO_2$ and $H_2$. The catalyst undergoes cyclic regeneration. DE 198 58 747 A1 describes a similar process.

Heating the catalyst bed or implementing an isothermal operating mode permit high conversion rates in a bulk catalyst bed. The disadvantage of this method, however, is that such very high conversion rates can only be achieved at high temperatures on account of the position of thermodynamic equilibrium, which also entails a reduction of the selectivity.

The operating mode in the presence of water vapour as described above has the advantage that it reduces the partial pressure of hydrocarbons and consequently increases the conversion rate. Moreover, the use of steam helps to convert part of the hydrocarbon deposits on the catalyst to form $CO_2$ and to obtain prolonged intervals between the regeneration cycles. However, the addition of too much steam is disadvantageous since it causes a substantial increase in volume of the gas stream, which requires a larger amount of investment and deteriorates the process efficiency. Furthermore the danger of steam reforming of hydrocarbons increases, which entails product losses and/or decrease in yield. The amount of steam that can be added without encountering the said problems entirely depends on the absolute pressure of the reaction and on the dehydration catalyst used.

A further possibility to overcome the thermodynamic limitation of the conversion rate under equilibrium conditions is to selectively burn part of the hydrogen obtained by dehydration, i.e. by the addition of oxygen—termed SHC for "Selective Hydrogen Combustion"—and thereby shifting the dehydration equilibrium to a higher conversion rate. EP 0 799 169 B1, for example, describes a reactor for such a dehydration process combined with SHC, in which a paraffin/oxygen mixture is sent via a first catalyst suitable for dehydration as well as selective oxidation of hydrogen obtained, further oxygen being introduced into an intermediate chamber of the reactor, and a second catalyst likewise being provided for dehydration and selective oxidation of hydrogen obtained. The process in accordance with EP 0 799 169 B1 takes place in an autothermal mode, the exothermic reaction of hydrogen with oxygen supplying the energy required to carry out the endothermic dehydration reaction (1).

Furthermore, document WO 96/33150, for example, describes a process in which the paraffin mixture is first dehydrated in a first step, oxygen being subsequently added and, at least, a second step is provided for making this oxygen react with the hydrogen released by dehydration in order to form water vapour. At least one part stream of the product obtained undergoes post-dehydration so that non-reacted paraffins can be dehydrated. It is also suggested that a return stream to the first step be installed.

These two processes have the disadvantage that the addition of oxygen and the exothermic selective oxidation of hydrogen cause very high temperatures, a fact that entails a reduction of the selectivity of catalytic dehydration.

The problem of overheating the hydrogen oxidation and with it the downstream dehydration can be solved by arranging an intercooler upstream of the selective hydrogen oxidation to reduce the inlet temperature of the second catalyst bed. Document U.S. Pat. No. 4,599,471, for example, suggests such an inter-cooling which may be of the indirect or direct type. Direct cooling can be carried out with the aid of inert gases, such as nitrogen, helium etc. or steam.

Temperature adjustment, however, by indirect cooling is a demerit because it requires a firm heat exchanger installation, which does not permit a specific temperature control of the catalyst bed regeneration, or it is necessary to install a device for temporary uncoupling of the heat exchangers, for example, by means of a by-pass that can be shut off by a valve. The latter solution would be a rather expensive configuration in view of the large pipe cross-sections and the high operating temperature of about 500° C. to 650° C. due to the dehydration. Direct cooling by inert gas is a real demerit because such gases would later have to be separated from the product in costly process steps during product makeup. Direct cooling using steam is a disadvantage as steam is not inert in the reaction (as described above) and because the cooling measure entails a certain steam-to-hydrocarbon ratio depending on the type of cooling. An intense cooling thus substantially increases the amount of steam, which is detrimental to the process.

Document WO 2004/039920 also describes a process in which water as well as water vapour are added for the reason indicated above. All of the processes named here are not suitable for the use of propane sources that are contaminated by oxygen or other gas components without performing a previous treatment of the propane stream from such a source, because otherwise heating the input stream which contains propane and oxygen to the reactor inlet temperature would already trigger off a non-catalytic and thus non-selective reaction of the oxygen with propane, thus causing loss of product yield.

A further demerit of all processes described here consists in the fact that hydrogen is present in the product stream of the process. For a later exploitation of the olefin product, the hydrogen must be separated in a relatively sophisticated and expensive gas separation step. This is a specific disadvantage when the olefin product is exploitable at a comparatively low degree of purity, i.e. if the gas treatment process can be performed in a very simple manner to satisfy any other requirement.

BRIEF SUMMARY OF THE INVENTION

The objective of the invention, therefore, is to provide a process configuration for the dehydration with an optional hydrogen oxidation which permits the exploitation of a propane source contaminated with oxygen and even with other gas components. A further aim of the invention is to eliminate hydrogen obtained by dehydration, to a large extent or almost completely by means of oxidation, yet without impairing the propylene selectivity. This allows to abandon any expensive hydrogen separation.

As stated in the main claim, the aim of the invention is solved as follows:

A first gas mixture with a min. temperature of 400° C., preferably 500° C., technically oxygen-free but with a content of propane, water vapour and hydrogen, is fed to a reaction device having at least one catalyst bed and exhibiting the standard dehydration conditions;

A further gas mixture containing propane and oxygen and which also may have a content of ammonia, the propane content exceeding that of oxygen, is likewise fed to the said reaction device, in which the said mixture reacts with the first gas mixture, thereby forming propylene, water vapour and hydrogen;

The gas mixture thus obtained and containing propylene, propane, water vapour and hydrogen is subsequently withdrawn from the reaction device.

In this case, the term "technically oxygen-free gas" is understood to mean a gas that complies with the standard specifications and whose content of oxygen, especially that of molecular oxygen $O_2$, is below 100 ppm. Commercial propane obtained by petroleum and natural gas extraction is normally "technically oxygen-free" within the meaning of the present invention.

In an embodiment of the invention, superheated water vapour is added to the first gas mixture prior to being fed to the said reaction device. This method permits a control of the energy balance via the reaction device, whenever the cooler gas mixture with a content of propane and oxygen has a higher propane portion than the warmer gas mixture with a content of propane, water vapour and hydrogen, yet without the need for heating the latter to too high a temperature, i.e. in excess of 550° C., because this procedure would entail a non-selective reaction of propane with water vapour.

According to a further embodiment of the invention, at least part of the gas mixture obtained and containing propylene, propane, water vapour and hydrogen is added to a gas mixture, thus forming the first gas mixture with a content of propane, water vapour and hydrogen and being fed to the reaction device at a min. temperature of 400° C. This is a loop performance because the dehydration process takes place only in an incomplete manner on account of the chemical equilibrium gradually obtained.

A further embodiment of the present invention provides for a reaction device formed by two series-connected catalyst beds, each of them being individually fed with the further gas mixture containing propane and oxygen and the amount of oxygen added being under-stoichiometric compared to the amount of hydrogen added, i.e. in relation to the reaction of oxygen with hydrogen to form water vapour.

According to a further embodiment of the invention, the reaction device consists of three series-connected catalyst beds, the first two of them being individually fed with the further gas mixture containing propane and oxygen, the amount of oxygen added being under-stoichiometric compared to the amount of hydrogen added in the first two beds, i.e. in relation to the reaction of oxygen with hydrogen to form water vapour, and the third catalyst bed being fed with an oxygen-bearing gas, which in this case may be the further gas mixture containing propane and oxygen or contain a part thereof, and the amount of oxygen added being stoichiometric compared to the amount of hydrogen added, i.e. in relation to the reaction of oxygen with hydrogen to form water vapour.

The two latter embodiments primarily differ from the others in that a third step is added to the process. If a type of loop is provided, the withdrawal of the product stream can take place either downstream of the first or second catalyst bed. When returning the reaction mixture from the first or second step, it is easy to separate the water vapour with the aid of condensation.

The individual catalyst beds may be partitioned or split up into several vessels, yet maintaining the same type of connection. Furthermore, it is possible to connect in parallel several small catalyst beds that behave like one big catalyst bed. The term "catalyst bed" is understood to mean in this context that such variants are logically just one catalyst bed within the meaning of this invention.

In a further embodiment of this invention, $H_2O$ is added as water or steam or a mixture thereof at a point located between the first and the second beds connected in series. As a rule, a defined ratio of $H_2O$ and hydrocarbons is specified, irrespective of their physical state; this very specific setting of the ratio of $H_2O$ and hydrocarbons in the gas phase avoids a disadvantageous amount of vapour/steam in the process, in particular steam reforming or too large a volumetric rate of gas flow due to a surplus steam or too much hydrocarbon deposit on the catalyst due to lack of steam.

Prior to entering the third catalyst bed the reaction mixture must be cooled down by direct or indirect heat exchange in order to reduce the temperature at which the hydrogen oxidation is carried out. This method precludes a non-selective hydrogen oxidation, which otherwise would reduce the propylene yield. In a further embodiment of the invention, a complete oxidation of the hydrogen takes place in the third catalyst bed at a temperature ranging from 200 to 500° C., preferably from 300 to 400° C.

The input gas mixture containing propane and oxygen, which also may have a content of ammonia, the propane content exceeding that of oxygen, and which is fed to the same reaction device in which it reacts with the first gas mixture, thereby forming propylene, water vapour and hydrogen, can be taken from industrial plants for the production of acrylonitrile or propylene oxide or acrolein or acrylic acid, in which the said mixture is obtained. In the case of combined application, it is possible to abandon some of the purification steps, which is a benefit of the invention.

Any embodiment of the present invention provides for standard dehydration catalysts used in all catalyst beds. There are, for example, Pt and Sn-bearing catalysts supported by Zn aluminate, Ca aluminate or hydrotalcite. Moreover, any commercial dehydration catalyst is suitable for the catalyst beds of each step, as singleton or a special catalyst, for hydrogen oxidation which permits better selectivity than that of standard dehydration catalysts in the hydrogen oxidation, in combination with a standard dehydration catalyst.

BRIEF DESCRIPTION OF THE DRAWINGS

The invention is illustrated below on the basis of two examples.

DETAILED DESCRIPTION OF THE INVENTION

Figure 1:
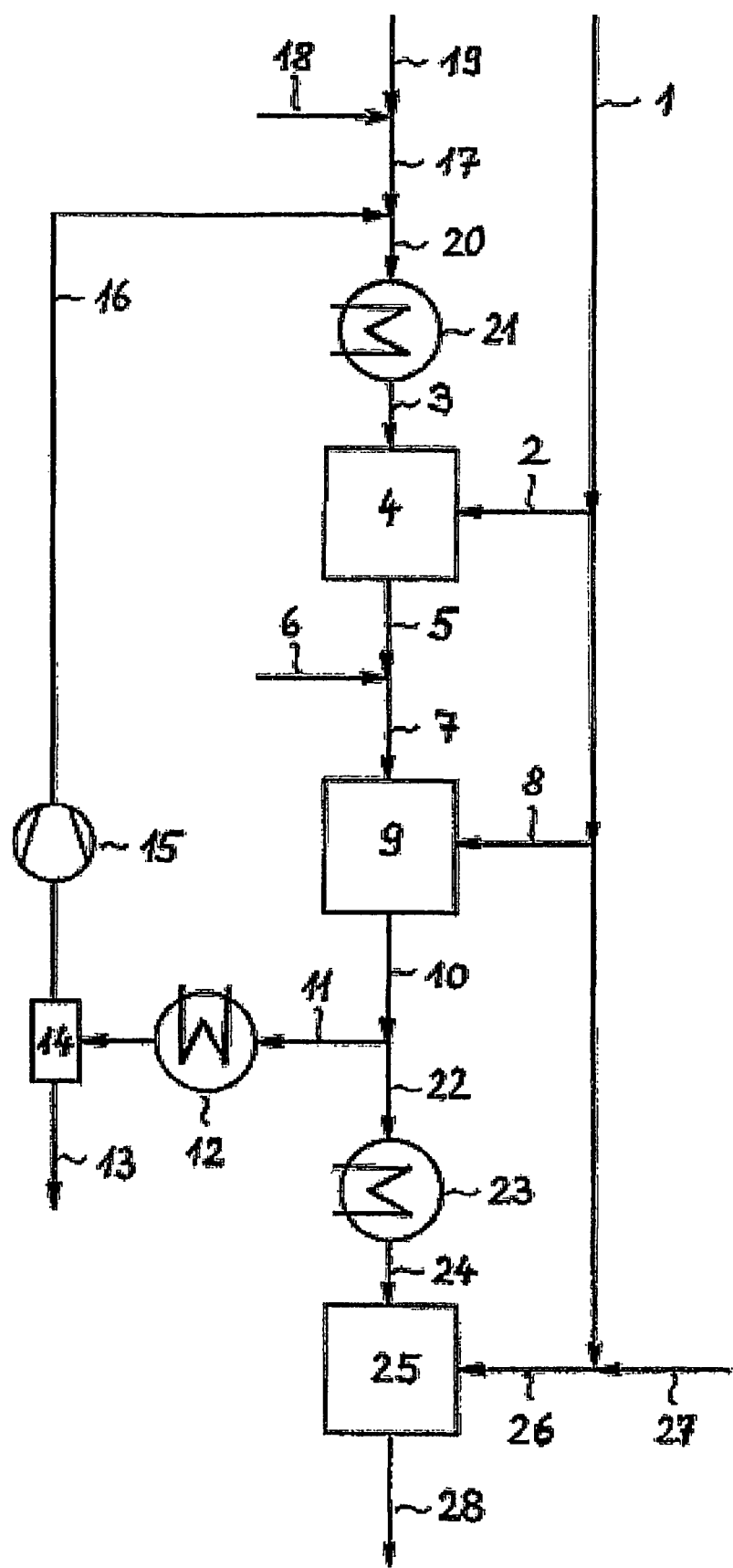
FIG. 1 showing the process in line with the invention, with two oxidehydration reactors for propylene and an oxidation reactor for hydrogen.

FIG. 1: First part stream 2 is withdrawn from input mixture 1 that contains propane and small portions of oxygen, carbon dioxide, methane, ethane and traces of hydrocarbons, the said stream 2 then being piped, together with loop gas 3, to first oxidehydration reactor 4 in which part of the mixture reacts at a temperature of 500 to 600° C.

Reaction gas 5 withdrawn from first oxidehydration reactor 4 is mixed with steam/water mixture 6, thus obtaining gas mixture 7. Together with second part stream 8 withdrawn from input gas 1, gas mixture 7 is fed to second oxidehydration reactor 9, in which a further reaction takes place at 500 to 600° C.

Part of gas stream 10 obtained and rich in propylene and hydrogen is withdrawn as recycle gas 11, which is cooled in recycle gas cooler 12 and upon separating aqueous condensate 13 in condensate trap 14, the said recycle gas is subsequently returned to first oxidehydration reactor 4 by means of loop gas compressor 15. This method permits the addition of mixture 17 (of steam 18 and propane 19) to loop gas 16, whereupon loop gas 20 is heated to approx. 400° C. in heater 21 prior to being fed as loop gas 3 to first oxidehydration reactor 4.

Gas 22 leaving the second oxidehydration reactor and containing the remaining propylene-rich portion is cooled to approx. 300° C. in gas cooler 23 and cooled gas 24 is fed to hydrogen combustion reactor 25, in which the hydrogen contained is selectively burnt at 300 to 400° C., together with residual part stream 27 enriched with oxygen 26 of input gas 1. Product gas 28 leaving hydrogen combustion reactor 25 can subsequently be subjected to heat recovery and gas separation or used as feed gas for synthesis processes.

All oxidehydration reactors contain at least one catalyst bed, the catalyst installed being a standard dehydration catalyst normally used in all oxidehydration reactors or dehydration steps.

Figure 2:
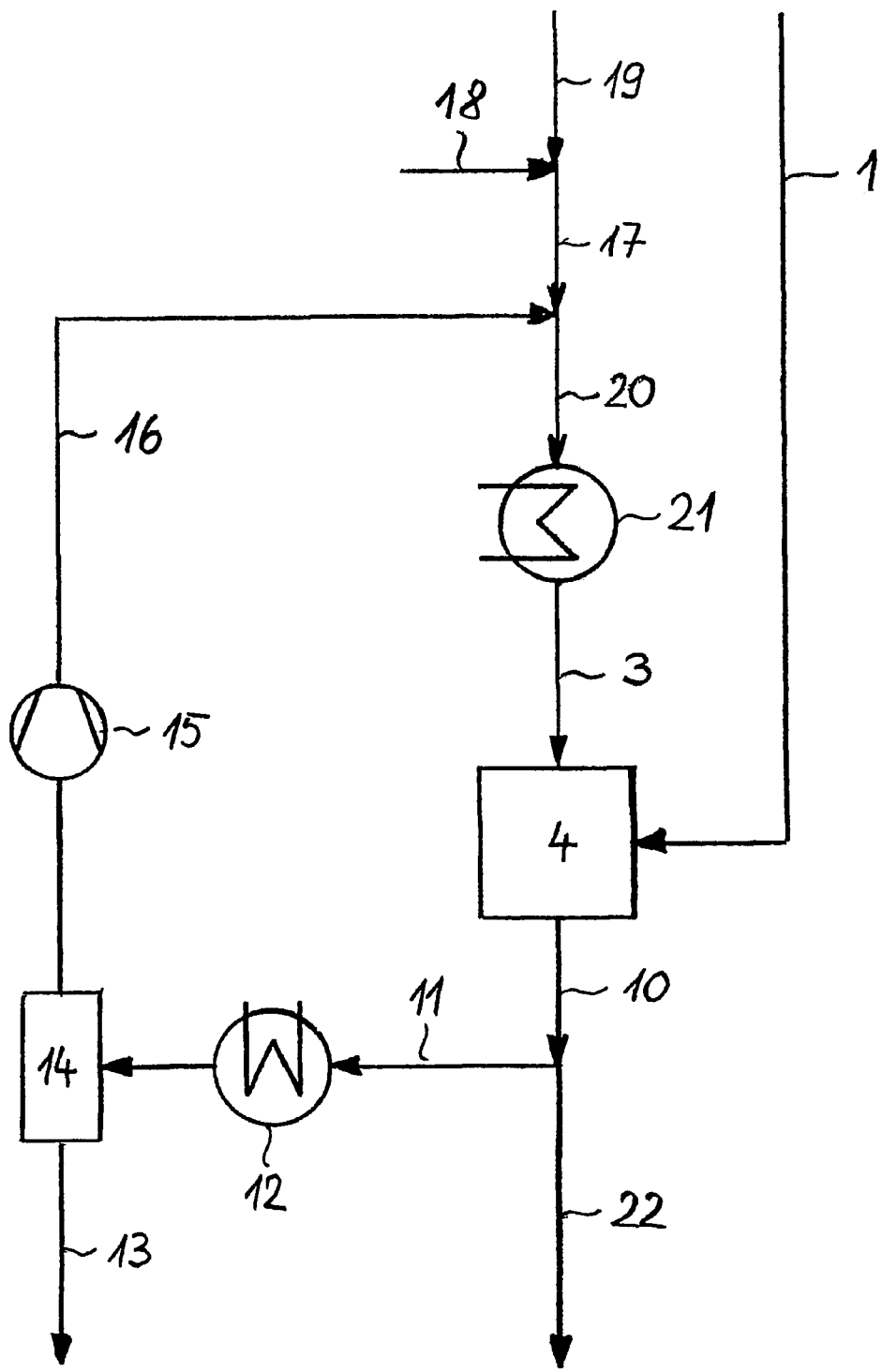
FIG. 2 depicts the inventive process with an oxidehydration reactor for propylene.

FIG. 2: Input mixture 1 that contains propane and small portions of oxygen, carbon dioxide, methane, ethane and traces of hydrocarbons, is piped, together with loop gas 3, into oxidehydration reactor 4, in which part of the mixture reacts at a temperature of 500 to 600° C. From gas 10 obtained and rich in propylene and hydrogen, a portion of recycle gas 11 is withdrawn and cooled in recycle gas cooler 12 and upon separation of aqueous condensate 13 in condensate trap 14, it is returned to oxidehydration reactor 4 by means of loop gas compressor 15. This method permits the addition of mixture 17 (of steam 18 and propane 19) to loop gas 16, whereupon loop gas 20 is heated to approx. 500° C. in heater 21 prior to being fed as loop gas 3 to first oxidehydration reactor 4.

For further illustration of the process according to the embodiment shown in FIG. 1, refer to the example of calculation below, the gas components being indicated in kmol/h and no consideration being attached to gas components lower than 0.1 kmol/h. The numbering of the streams complies with FIG. 1.

Example of Calculation 1

| Stream No. | | 2 | 7 | 8 | 16 |
|---|---|---|---|---|---|
| Temperature | [° C.] | 200 | 400 | 200 | 40 |
| Hydrogen $H_2$ | [kmol/h] | 0.0 | 15.0 | 0.0 | 8.1 |
| Propane $C_3H_8$ | [kmol/h] | 15.3 | 50.3 | 29.1 | 23.9 |
| Propylene $C_3H_6$ | [kmol/h] | 0.0 | 18.4 | 0.0 | 10.0 |
| Oxygen $O_2$ | [kmol/h] | 1.9 | 0.0 | 3.7 | 0.0 |
| Methane $CH_4$ | [kmol/h] | 0.4 | 2.1 | 0.7 | 1.3 |
| Ethane $C_2H_6$ | [kmol/h] | 0.1 | 0.3 | 0.1 | 0.2 |
| Carbon dioxide $CO_2$ | [kmol/h] | 0.9 | 4.4 | 1.7 | 2.8 |
| Steam/water $H_2O$ | [kmol/h] | 0.0 | 341.6 | 0.0 | 0.0 |

| Stream No. | | 17 | 24 | 27 | 28 |
|---|---|---|---|---|---|
| Temperature | [° C.] | 200 | 300 | 200 | 400 |
| Hydrogen $H_2$ | [kmol/h] | 0.0 | 15.0 | 0.0 | 0.0 |
| Propane $C_3H_8$ | [kmol/h] | 20.0 | 44.4 | 32.1 | 76.5 |
| Propylene $C_3H_6$ | [kmol/h] | 0.0 | 18.6 | 0.0 | 18.6 |
| Oxygen $O_2$ | [kmol/h] | 0.0 | 0.0 | 7.5 | 0.0 |
| Methane $CH_4$ | [kmol/h] | 0.0 | 2.5 | 0.8 | 3.3 |
| Ethane $C_2H_6$ | [kmol/h] | 0.0 | 0.4 | 0.1 | 0.5 |
| Carbon dioxide $CO_2$ | [kmol/h] | 0.0 | 5.2 | 1.8 | 7.0 |
| Steam/water $H_2O$ | [kmol/h] | 241.4 | 219.7 | 0.0 | 234.7 |

For further illustration of the process according to the embodiment shown in FIG. 2, refer to the example of calculation below, the gas components being indicated in kmol/h and no consideration being attached to gas components lower than 0.1 kmol/h. The numbering of the streams complies with FIG. 2.

Example of Calculation 2

| Stream No. | | 1 | 10 | 11 | 17 |
|---|---|---|---|---|---|
| Temperature | [° C.] | 350 | 510 | 510 | 200 |
| Hydrogen $H_2$ | [kmol/h] | 0.0 | 24.7 | 8.9 | 0.0 |
| Propane $C_3H_8$ | [kmol/h] | 78.6 | 122.9 | 44.2 | 20.0 |
| Propylene $C_3H_6$ | [kmol/h] | 0.0 | 30.0 | 10.8 | 0.0 |
| Oxygen $O_2$ | [kmol/h] | 3.8 | 0.0 | 0.0 | 0.0 |
| Methane $CH_4$ | [kmol/h] | 1.1 | 2.8 | 1.0 | 0.0 |
| Ethane $C_2H_6$ | [kmol/h] | 0.2 | 0.5 | 0.2 | 0.0 |
| Carbon dioxide $CO_2$ | [kmol/h] | 2.6 | 6.4 | 2.3 | 0.0 |
| Steam/water $H_2O$ | [kmol/h] | 0.0 | 243.7 | 87.7 | 246.6 |

KEY TO REFERENCED NUMBERS

1 Input mixture
2 $1^{st}$ part stream
3 Loop gas
4 $1^{st}$ oxidehydration reactor
5 Reaction gas
6 Steam/water mixture
7 Gas mixture
8 $2^{nd}$ part stream
9 $2^{nd}$ oxidehydration reactor
10 Propylene and hydrogen-rich gas
11 Recycle gas
12 Recycle gas cooler
13 Aqueous condensate
14 Condensate trap
15 Loop gas compressor
16 Loop gas
17 Mixture

18 Steam
19 Propane
20 Loop gas
21 Heater
22 Propylene rich gas
23 Gas cooler
24 Cooled gas
25 Hydrogen combustion reactor
26 Oxygen
27 Residual part stream
28 Product gas

The invention claimed is:

1. A process for the production of propylene from propane comprising the steps of:
   a first gas mixture with a minimum temperature of 400° C., technically oxygen-free but comprising propane, water vapor and hydrogen, is fed to a reaction device having at least one catalyst bed and exhibiting the standard dehydration conditions;
   a further gas mixture containing propane and oxygen and optionally a content of ammonia, the propane content exceeding that of oxygen, is likewise fed to the said reaction device, in which the said mixture reacts with the first mixture, thereby forming propylene, water vapor and hydrogen forming a further gas mixture; and
   the further gas mixture thus obtained and containing propylene, propane, water vapor and hydrogen is subsequently withdrawn from the reaction device.

2. The process according to claim 1, wherein superheated water vapor is added to the first gas mixture prior to being fed to the said reaction device.

3. The process according to claim 1, wherein at least part of the gas mixture obtained and containing propylene, propane, water vapor and hydrogen is added to a gas mixture, thus forming the first gas mixture with a content of propane, water vapor and hydrogen and being fed to the reaction device at a minimum temperature of 400° C.

4. The process according to claim 1, wherein the first technically oxygen-free gas mixture is fed to a reaction device at a minimum temperature of 500° C., the reaction device having at least one catalyst bed and exhibiting the standard dehydration conditions.

5. The process according to claim 1, wherein the reaction device comprises two series-connected catalyst beds, each of them being individually fed with the further gas mixture containing propane and oxygen, and the amount of oxygen added being under-stoichiometric compared to the amount of hydrogen added.

6. The process according to claim 1, wherein the reaction device consists of three series-connected catalyst beds, the first two of them being individually fed with the further gas mixture containing propane and oxygen, and the amount of oxygen added being under-stoichiometric compared to the amount of hydrogen added in the first two beds, and the third catalyst bed being fed with an oxygen-bearing gas, which in this case may be the further gas mixture containing propane and oxygen or contain a part thereof, and the amount of oxygen added being stoichiometric compared to the amount of hydrogen added.

7. The process according to claim 5, wherein the first and the second catalyst beds connected in series are fed with water or steam or a mixture thereof.

8. The process according to claim 6, wherein a complete oxidation of the hydrogen takes place in the third catalyst bed at a temperature ranging from 200 to 500° C.

9. The process according to claim 6, wherein a complete oxidation of the hydrogen takes place in the third catalyst bed at a temperature ranging from 300 to 400° C.

* * * * *